| United States Patent [19] | [11] Patent Number: 4,582,709 |
| Peters et al. | [45] Date of Patent: Apr. 15, 1986 |

[54] CHEWABLE MINERAL SUPPLEMENT

[75] Inventors: David Peters, Long Valley; John Denick, Jr., Newton, both of N.J.

[73] Assignee: Warner-Lambert Company, Morris Plains, N.J.

[21] Appl. No.: 699,692

[22] Filed: Feb. 8, 1985

[51] Int. Cl.$^4$ .............................................. A23L 1/304
[52] U.S. Cl. .................................... 426/74; 426/659; 426/660; 424/154
[58] Field of Search ................... 426/74, 285, 72, 272, 426/660, 800, 804, 806, 810, 648, 656, 659, 658; 424/128, 145, 147, 154, 153

[56] References Cited

U.S. PATENT DOCUMENTS

| 2,926,121 | 2/1960 | Hobbs | 424/155 |
|---|---|---|---|
| 4,327,076 | 4/1982 | Puglia et al. | 426/660 |
| 4,327,077 | 4/1982 | Puglia et al. | 426/660 |
| 4,425,332 | 1/1984 | James | 424/154 |
| 4,545,989 | 10/1985 | Becker | 424/154 |

FOREIGN PATENT DOCUMENTS 1165616  9/1982  Canada .

OTHER PUBLICATIONS

Alikonis, 1979, Candy Technology pp. 1-2 and 100-107, AVI Publishing Co. Westport, CT.
Physicians Desk Reference, 1981, p. 1352, Medical Economics Co., Oradell, NJ.
Bellups et al., 1983, American Drug Index, p. 556, Lippencott Co., Philadelphia, PA.
Pike et al., 1975, Nutrition: An Integrated Approach 2nd edition pp. 156 and 180, John Wiley & Sons, New York.

*Primary Examiner*—Raymond N. Jones
*Assistant Examiner*—Carolyn Paden
*Attorney, Agent, or Firm*—Charles A. Gaglia, Jr.; Gary M. Nath

[57] ABSTRACT

A chewable mineral supplement and process for making the same. The product comprises from about 3 to about 40% by weight of mineral compound, and from about 1.5 to about 6% by weight edible polyol admixed in a soft, nougat candy base.

32 Claims, No Drawings

CHEWABLE MINERAL SUPPLEMENT

BACKGROUND OF THE INVENTION

1. Field of the Invention:

This invention relates to a mineral supplement in a chewable, edible, soft candy base. More particularly, the invention pertains to a novel form of mineral supplement which contains inorganic and organic salts of elements essential to human nutrition and health. The invention also relates to the method by which these mineral supplements may be prepared.

Most particularly, the invention relates to a novel, soft candy which contains calcium carbonate as the mineral supplement for dietary calcium.

2. Description of the Prior Art:

The use of mineral supplements to treat human illness is well known. A variety of illnesses are caused by specific mineral deficiencies. Mineral deficiencies have also been known to cause a variety of illnesses in humans. Several of these are discussed below.

A deficiency in calcium levels may result in convulsions, tetany, behavioral and personality disorders, mental and growth retardation, and bone deformaties.

Phosphorous is essential for most metabolic processes. Symptoms of phosphate deficiency include weakness, anorexia, bone demineralization, and hypocalcemia.

Magnesium is essential for the functioning of a number of critical enzymes including enzymes involved with ATP-dependent phosphorylation, protein synthesis, and carbohydrate metabolism. Magnesium deficiency also causes apathy, depression, increased CNS stimulation, delirium, and convulsions.

Lithium has been found useful in the treatment of manic-depressive illness, as a mood stabilizer, and as an antidepressive.

Sodium in the form of salts (sodium chloride) plays the major role in control of distribution of water in the body. Salt deficiency results in a diminution in extracellular space, and induces profound changes in the circulatory system. Salt deficiency leads to symptoms such as mental depression with drowsiness, apathy, anorexia, nausea and vertigo.

Potassium is the important cationic constituent of the intracellular fluid. Potassium deficiency may result in kidney damage with vacuolization of the collection tubules. Potassium deficiency is characterized by mental changes (hallucinations, loquacity) an animated facial expression and limpness of the extremities. The muscles become soft and weak.

Iron plays an important role in oxygen and electron transport. Symptoms of iron deficiency are fatigability, weakness and lassitude. Other symptoms of anemia include pallor, dyspnea on exertion, palpitation and a feeling of exhaustion.

Zinc activates a number of enzymes concerned in protein metabolism as well as some enolases and lecithinases. There is evidence to suggest that zinc deficiency may cause dwarfism and hypogonadism.

A general discussion of the the rapeutic uses of mineral compounds may be found in A. Grollman & E. F. Grollman, *Pharmacology and Therapeutics,* 7th Ed. Lea & Febiger, Philadelphia, Pa. at pages 858–873, 876, 877, 907–915.

A large number of commercial products are available which contain mineral supplements. Most of these products are available as combination products with vitamins. Iron supplements are generally an exception as a number of iron supplements are available as a single mineral supplement.

Mineral supplements are available in multivitamin tablets, capsules, powders, liquids and hard chewable tablet formulations. Chewable tablets have been used to overcome the dosage form size problem which results from the necessity to use large quantities of mineral salts to treat mineral deficiencies. For example, calcium deficiencies are treated with average daily doses which range from 1 to 3 grams when calcium phosphate and calcium carbonate are the calcium source to as much as 15 grams daily when calcium gluconate is the calcium source.

Hard chewable tablets offer the ability to deliver large doses of mineral supplements, however, the resultant products have a gritty mouthfeel and a taste dominated by the often salty, or bitter taste of the mineral compound.

Chewable dosage forms containing large amounts of calcium compounds have been developed in the area of antacids. Exemplary tablets contain 500 mg. to 750 mg of calcium carbonate. Non-chewable calcium supplement tablets are also known to contain 375 mg. of calcium carbonate per tablet to 1200 mg of calcium as calcium carbonate.

Canadian Pat. No. 1,165,616 to Becker, et al. discloses a soft nougat type antacid composition. The Becker, et al. product may contain calcium carbonate up to about 20% by weight as the antacid compound. To prepare a non-chalky nougat based product, Becker, et al. requires the addition of antacid to the frappe (whipped) portion of the soft candy composition. The chalky in mouth taste is avoided by coating the antacid particles having a size up to 1.5 microns with the frappe mixture prior to forming the nougat.

While the products described above may be able to deliver mineral supplements, they suffer from a variety of consumer acceptance problems. The chewable tablets are large and generally leave a chalky and or gritty sensation in the mouth. Non-chewable tablets and capsules require multiple unit dosages, i.e., 2 to 4 tablets or capsules per administration. More potent non-chewable tablets or capsules are physically so large as to be objectionable to the consumer.

The soft chewable product of Becker, et al. overcomes the taste and mouthfeel problems of hard chewable tablets. Like the smaller dose non-chewable tablets, the Becker, et al. product would require multiple dosage administration. In addition, production of the Becker, et al. product requires mineral compounds having a particle size of less than 1.5 micrometers.

It would, therefore, be desirable to develop a pleasant tasting, soft, chewable mineral supplement capable of delivering effective amounts of mineral supplements.

SUMMARY OF THE INVENTION

A procedure for preparing a soft, chewable mineral supplement which may contain up to 40% by weight mineral compound has been unexpectedly discovered. This has been achieved by incorporating an edible polyol and a mineral compound into a soft, nougat candy base to form a soft, chewable mineral supplement having no chalky or gritty mouthfeel.

DETAILED DESCRIPTION

In particular, it has been found that a chewable mineral supplement having a penetration hardness of 2 mm or more, and a final water content of about 2 to about 4.5% by weight is produced from an admixture of about 40 to about 85% by weight of a nougat candy base having a sugar to corn syrup ratio from about 1:1 to about 2:1 wherein said corn syrup has a dextrose equivalence of about 35 to about 55; an edible polyol in an amount of from about 1.5 to about 6.0% by weight; a mineral compound in an amount up to about 40% by weight; and optimally a graining compound in an amount from about 0.5 to about 4% by weight.

While the invention is not to be limited to theoretical considerations, it is believed that incorporation of an edible polyol such as glycerin into the soft nougat candy base provides an unexpected coating action. This coating action permits the otherwise dry, chalky, gritty particulate mineral compounds to be incorporated into the candy base such that each particle becomes coated by the candy base. It is believed that this candy base coating prevents the chalky, gritty taste and mouthfeel generally associated with chewable mineral supplements and antacids.

Glycerin is known in the confectionery art as a humectant and conditioner. The humectant qualities of glycerin are used to prevent confectionery products from drying out during low humidity conditions. Surprisingly, a very small change in glycerin content has a large effect on the Equilibrium Relative Humidity (ERH) of the inventive product. The ERH is the relative humidity at which the product will neither gain nor lose water to the atmosphere. When the glycerin content of the inventive product is 3.6% by weight, the ERH is 46%. When the glycerin content is 4.1%, the ERH is 38%. This relatively low ERH enables the final product to retain its soft texture.

The incorporation of large quantities of powders into a nougat base causes rapid product graining. This graining causes processing difficulties and a short, granular product chew. Incorporation of glycerin into the nougat base unexpectedly permits large quantities of powder to be admixed into the nougat base, without causing graining or a granular chew. The addition of glycerin further, unexpectedly eliminates processing difficulties.

The nougat candy base of the present invention comprises a syrup component and a whipped component. The syru component comprises by weight of the chewable mineral supplement, corn syrup in an amount of about 13 to about 41% having a dextrose equivalence from about 35 to about 55, and sugar in an amount of about 15 to 53%. Corn syrup having a dextrose equivalence less than 35 will cause the nougat base to become too hard, dry and less pliable. A dextrose equivalence greater than 55 will cause the nougat base to become discolored, sticky and difficult to process.

In a preferred embodiment, the syrup component comprises by weight of the chewable mineral supplement from about 15 to about 30% corn syrup having a dextrose equivalence from about 35 to about 55, and sugar in an amount from about 20 to about 40%.

One important feature of the invention is the weight ratio of sugar to corn syrup solids. This ratio may be about 1:1 to about 2:1, preferably about 1.2:1 to about 2:1 and most preferably about 1.3:1 to about 1.7:1. A sugar to corn syrup ratio of less than 1:1 produces a final product having texture that is too soft and sticky which results in sticky mouthfeel. A sugar to corn syrup ratio greater than 2:1 produces a grainy textured product which is difficult to chew.

In a more preferred embodiment, the syrup component comprises by weight of the chewable mineral supplement from about 18 to about 21% corn syrup having a dextrose equivalence from about 35 to about 55, and sugar in an amount of about 27 to about 31%.

The whipped component comprises by weight of the chewable mineral supplement, at least one whipping agent present in an amount of from about 0.1 to about 1%. The whipping agent functions as a means of holding air introduced into the product to produce a uniform dispersity of air cells within the confection leading to a lower specific weight and considerable modification to the texture.

Suitable whipping agents may include egg albumen, gelatin, milk proteins or other milk derived compounds such as whey, casein derivatives, vegetable proteins such as soy derived compounds, modified milk proteins, and mixtures thereof.

In a preferred embodiment, the whipped component comprises, by weight of the chewable mineral supplement at least one whipping agent present in an amount of from about 0.2 to about 0.6% and;most preferably 0.3 to about 0.4% and other conventional components such as sugar, sorbitol, starch, water, glucose syrup and so forth.

The edible polyol may be selected from the group consisting of propylene glycol, glycerin, polyethylene glycol and mixtures thereof. Preferably, the edible polyol comprises glycerin.

In a preferred embodiment, the edible polyol is present in an amount from about 2 to about 5% by weight of the chewable mineral supplement and most preferably in an amount from about 2.5 to about 4.5% by weight. A polyol content of less than 2% results in a chalky tasting, dry product. Polyol content greater than 5% results in a sticky, difficult to process product having unpleasant sticky chew characteristics.

The mineral compound may be selected from a wide range of compounds that provide a source of absorbable minerals when ingested. Suitable compounds are preferably organic or inorganic salts that render the compounds absorbable herein. Exemplary salts may be selected from the group consisting of salts of lithium, sodium, potassium, magnesium, calcium, phosphorous, iron, zinc and mixtures thereof.

One particularly preferred mineral compound is calcium which calcium compound may be selected from the group consisting of calcium gluconate, calcium chloride, calcium lactate, calcium phosphate, monobasic calcium phosphate, dibasic calcium phosphate, tribasic calcium phosphate, calcium carbonate, calcium tartrate, calcium glycerophosphate, calcium levulinate, calcium hypophosphate, calcium sulfate, calcium gluceptate, calcium chelates, calcium amino acid chelate, ground limestone, ground oyster shells and mixtures thereof. Preferably the calcium compound comprises calcium carbonate.

Compounds used to provide a mineral supplement of lithium include organic and inorganic salts wherein the anion is chloride, carbonate, citrate, sulfate, bromide and mixtures thereof.

Compounds useful in providing a mineral supplement of zinc include inorganic and organic salts wherein the anionic portion of the salt is carbonate, chloride, citrate, and mixtures thereof.

Compounds useful in providing a mineral supplement of phosphorous include salts wherein the anionic portion is a phosphate and the cationic portion is sodium, potassium, magnesium, iron, calcium, lithium, zinc and and mixtures thereof.

Compounds useful in providing a mineral supplement of potassium include inorganic and organic salts wherein the anionic portion of the salt is acetate, bicarbonate, bitartrate, bromide, carbonate, chloride, citrate, gluconate, phosphate monobasic, phosphate dibasic, phosphate tribasic, sulfate, tartrate and mixtures thereof.

Compounds used to provide a mineral supplement of iron include organic and inorganic salts and chelates of iron such as reduced iron, ferrous sulfate, iron ammonium citrate, ferrous carbonate, ferrous chloride, ferrous fumarate, ferroglycine sulfate, ferronascin, ferrous carbonate mass, ferrous carbonate saccharated, ferrous citrate, ferrous gluconate, ferrous lactate, ferrous sulfate, ferrous succinate, iron cheates, iron chelate with magnesium trisilicate and mixtures thereof.

Compounds used to provide a mineral supplement of sodium include organic and inorganic salts of sodium wherein the anionic portion of the salt is acetate, ascorbate, bicarbonate, carbonate, chloride, citrate, hypophosphite, lactate, phosphate monobasic, phosphate dibasic, phosphate tribasic, sulfate, tartarate and mixtures thereof.

Compounds used to provide a mineral supplement of magnesium include organic and inorganic salts of magnesium wherein the anionic portion of the salt is acetate, carbonate hydroxide, chloride, citrate, dibasic citrate, hydroxide, lactate, oxide, phosphate monobasic, phosphate dibasic, trisilicate, sulfate as well as the composition formed as the co-precipitated gel of aluminum hydroxide and magnesium carbonate, aluminum magnesium silicate, aluminum magnesium hydroxide and mixtures thereof.

The mineral compounds are incorporated into the present soft chewable products in particulate form. The particle size may vary widely depending upon the particular mineral source but must be of an adequate size to enable incorporation into the nougat candy base without exhibiting a sandy mouthfeel. Exemplary particle size ranges when using calcium carbonate may be from about 0.8 micrometers to about 3.5 micrometers for calcium carbonate U.S.P., and further to about 15 micrometers for ground limestone which is natural calcium carbonate. Similar ranges may be used for the remaining mineral compounds. The mineral compound is present in an amount from about 3 to about 40%, and preferably about 15 to about 40% by weight of the chewable mineral supplement.

The lower limit for the mineral compound is determined by the minimum therapeutic dose. For the compounds considered herein, the lower limit is considered to be about 3% by weight. It is, however, possible to have lower mineral compound concentrations used in the inventive formulations. Mineral compound concentrations greater than about 40%, however, are not useable since they result in a dry, chalky, gritty product.

The present invention may optionally include absorption enhancers. Absorption enhancers are a group of compounds which facilitate more complete and/or more rapid absorption of the mineral compound by the human body. In the case of calcium, such absorption enhancers include but are not limited to vitamin D, lysine, arginine, calcitrol, lactose and mixtures thereof.

Preferred absorption enhancers for calcium are vitamin $D_2$, vitamin $D_3$ and mixtures thereof. An absorption enhancer for iron is ascorbic acid. The absorption enhancer may be used in varying amounts well within the perview of the ordinary skilled artisan. Amounts may vary from as low as about 1.25 micrograms per dose up to about 20% by weight of the dose depending on the particular enhancer.

The present invention may further include compounds such as antiflatulents to reduce a potential side effect of ingesting mineral supplements containing, for example, a gas producing anion such as carbonate or bicarbonate. A preferred antiflatulent is simethicone. The amounts used will vary depending upon the amount of gas that will be produced which varies upon the mineral compound and the amount of it used in the formulation. Such amounts may be readily determined by the ordinary skilled artisan. They may vary from about 15 mg to about 80 mg per dose.

The chewable mineral supplement in addition to the foregoing materials may also include further additives utilized conventionally to prepare nougat products. Thus the present soft, chewable products may include materials selected from pigments, colorants, oils, fats, preservatives, flavorings, and so forth, and mixtures of these in varying amounts.

Those materials incorporated and desirable to aid in the final processing of the soft, chewable nougat based product include fats, oils, preservatives, colorants and flavorings. Suitable fats and oils include fractionated fat, hydrogenated oils, partially hydrogenated oils, unsaturated oils, coconut oil, palm oil, palm kernel oil, cottonseed oil, safflower oil, sunflower oil, soy oil, corn oil and mixtures thereof. The term "fats" and "oils" are used interchangeably, although there may be differences as understood by the skilled artisan. "Fats" is generally a term to refer to the solid embodiment of the above-mentioned groups and "oils" refers to the liquid form.

A graining compound may also be optionally employed to promote faster setting times for the final product. The graining compound is selected from the group consisting of fondant sugar, sugar, sorbitol crystals, lactose and mixtures thereof. The graining compound, when used, is present in an amount from about 0.5% to about 4.0% by weight.

Suitable flavorings include natural and artificial flavors such as mints, peppermint, artificial vanilla, natural vanilla, cinnamon, various fruit flavors, both individual and mixed. The flavorings are generally utilized in amounts that will vary depending upon the individual flavor and may, for example range up to 1% by weight or higher.

The colorants used in the present invention include pigments such as titanium dioxide that are incorporated into the nougat candy base and may be incorporated therein in amounts of up to 1% or higher by weight. Also, the colorants may include other dyes suitable for food, drug and cosmetic applications, and known as F.D.&C. dyes and lakes. A full recitation of all F.D.&C. and D.&C. colorants and their corresponding chemical structures may be found in the Kirk-Othmer, *Encyclopedia of Chemical Technology*, at Volume 5, pages 857–884, which text is accordingly incorporated herein by reference.

The chewable mineral supplement of the invention can be prepared by conventional confectionery making procedures. Such procedures generally entail admixing the nougat candy base with the remaining ingredients until a homogenous admixture is obtained and then forming the resulting mixture into suitable shapes for storage. The preparation of the nougat candy base may be achieved by routine procedures well known to the ordinary skilled artisan. One preferred procedure involves preparation of the whipping component and blending with the syrup component.

The whipped component may be prepared by mixing the whipping agent with other desirable components. The whipped component is generally prepared from gelatin, egg albumen, milk proteins such as casein, and vegetable proteins such as soy protein, and the like which are added to a gelatin solution and rapidly mixed at ambient temperature to form an aerated sponge like mass.

The syrup component is prepared by initially mixing corn syrup, sugar component and an amount of water necessary to assure solution of the ingredients. The total water content is not critical, however, it is preferable to keep the initial water content below 40% by weight. This mixture is charged into a suitable cooker and cooked to a final water content of about 2% to about 11.0% by weight.

Once the above steps are complete, the whipped component and the syrup component may be combined, usually by the addition of whipped component to the syrup component after the syrup component's temperature has dropped to about 110° C. to about 118° C. The resultant combination is then mixed. At this point, the edible polyol is added. If colorants are to be incoporated, they may be incorporated into the candy base at this point. The composition is then mixed until a uniform homogenous mass is formed.

The mineral compound is then added and mixed until a uniform homogenous mass is again formed. If fats are to be incorporated, they are incorporated into the candy base at this time. The above composition is mixed until the temperature of the composition is less than about 90° C. but greater than about 60° C. At this point, the graining compound, if employed, is added to the composition. If flavorings are to be incorporated, they may be added into the candy base also at this time. The mixture is then further mixed until uniform.

Once all of the reagents have been blended into the mixture, the mixture is allowed to cool. The mixture may be cooled to ambient temperatures before final forming operations are completed.

A variety of final forming techniques may be utilized, depending upon the shape and size of the final product as desired.

Once prepared the final composition may be processed into any desirable shape or form to render the product suitable for providing the necessary amount of mineral compound. Exemplary, non-limiting shapes include squares, rectangles, spheres, tabloids and biconvex shapes. Other suitable shapes may also be employed.

The products of the invention must exhibit a soft chewable texture to be useable herein. The term "soft" as used herein with regard to the texture of the mineral supplement of the invention refers to a penetration hardness of greater than 2 mm. Products not exhibiting this property have been found to be unsuitable according to this invention. In particular, products exhibiting a hardness value less than 2 mm are not chewable and fall outside the scope of this invention. In contrast, products exhibiting complete penetration are considered too soft and tacky and will not maintain the product integrity sought herein.

The penetration hardness test procedure to determine penetration hardness involves the following:

The penetrometer hardness test employs a Precision Scientific Model 73510 Penetrometer equipped with a 3K-186 wax penetration needle having a diameter of 0.1 mm and a length of 3.8 cm.

The needle is placed into contact in the center of a square face perpendicular to the face. A 150 gram weight is applied to the needle for 5 seconds pressing the needle into the test piece. The penetration depth is measured and recorded in mm. The less penetration the harder the piece.

The present invention is further illustrated by the following examples. All parts and percentages in the examples and throughout the specification and claims are by weight of the final composition unless otherwise indicated.

EXAMPLE 1

This Example demonstrates the formation of a product of this invention.

The following ingredients were admixed in the order listed until a homogenous formulation was prepared after each step and until the final product was prepared. The final product was pressed into individual pieces having a weight of 4.5 grams and having a size of 11.5 mm × 1.94 mm × 1.94 mm.

The resulting structures were tested for hardness penetration and all had a hardness between 5 and 7 mm. When consumed, all of the products exhibited no chalky taste, and were soft in texture.

| Component | Percent by Weight of the Total Formulation |
|---|---|
| Nougat candy base having a syrup component with a 1.5:1 sugar to corn syrup ratio, water content 5% and a corn syrup component having a dextrose equivalence of 42 | 56.5 |
| Glycerin | 3.75 |
| Color (titanium dioxide) | 1.0 |
| Fat | 4.0 |
| Calcium carbonate | 33 |
| Graining compound (fondant sugar) | 1.5 |
| Flavor | 0.25 |
|  | 100.00 |

EXAMPLE 2

This Example demonstrates the formation of a product of this invention by modifying the water content of the syrup component of the nougat candy base.

The moisture content of the final chewable mineral supplement was varied by varying the moisture of the syrup component of the formulation given in Example 1.

| Test Run | % Moisture Content of Syrup | of Final Product | Product Description | Chew Characteristics |
|---|---|---|---|---|
| A | 6.0 | 4.5 | soft, tacky | soft, acceptable |
| B | 5.0 | 3.5 | soft, not tacky | acceptable |
| C | 4.0 | 2.5 | firm | firm, acceptable |
| D | 3.0 | 1.5 | hard | hard, un- |

| Test Run | % Moisture Content of Syrup | % Moisture Content of Final Product | Product Description | Chew Characteristics |
|---|---|---|---|---|
| | | | | acceptable |

The results indicate that final products having moisture contents from about 2.5 to about 4.5% by weight have acceptable chew and physical characteristics. Moisture contents below 2.0 were found to result in hard structures which exhibit excessive hardness and are unacceptable.

EXAMPLE 3

This Example demonstrates the effect of final product moisture content in relation to hardness as measured by the penetrometer test.

Test runs E to H were prepared in accordance with the formulation of Example 1. The total thickness of the final formed product is about 11.5 mm.

Products of this invention formed with a final product moisture content of 4.5% by weight or greater are too sticky and do not hold their shape.

| Test Run | Product Moisture Content | Penetration[1] (mm) | Product Observations |
|---|---|---|---|
| E | 5.0 | Complete | Very sticky cold flow |
| F | 4.1 | 10 to 11.5 | soft acceptable |
| G | 3.5 | 5 to 7 | soft acceptable |
| H | 2.8 | 2.5 to 3.5 | firm acceptable |

[1]Range of results on 3 determinations.

Test runs 1 to 4 were prepared in accordance with the formulation of Example 1. The total thickness of the final formed product is about 11.5 mm.

Products of this invention formed with a final product moisture content of 5% by weight or greater are too sticky and do not hold their shape.

EXAMPLE 4

This Example demonstrates the effect of glycerin content on the mineral supplement of this invention.

The procedure of Example 1 was repeated except that the glycerin content was varied as set forth below. The results are described in the table.

| Glycerin Content in Weight % | Product Characteristics |
|---|---|
| 5.0 | Soft texture Soft chew Tablet sticky |
| 3.75 | Smooth texture Firm chew Tablet not sticky |
| 2.75 | Slight chalkiness Dry chew Dry tablet |

EXAMPLE 5

This Example demonstrates the effect of modifying the sugar to corn syrup ratio of the syrup component of the nougat candy base in the mineral supplement of this invention.

The procedure of Example 1 was repeated except that the sugar to corn syrup ratio was varied as set forth below, the results are described in the table.

| Sugar/Corn Syrup Ratio Characteristics | Product |
|---|---|
| 1:1 | Soft sticky texture Sticky mouth feel Cold flow in processing Sticky |
| 1.2:1 | Good texture Good mouthfeel Acceptable processing Some tackiness |
| 1.5:1 | Good texture Good mouthfeel Acceptable processing Not tacky |
| 1.85:1 | Grainy texture Good mouthfeel Acceptable difficult to process Not tacky |

EXAMPLE 6

This Example demonstrates the effect of different mineral compounds.

The procedure of Example 1 was repeated except that the mineral compound was varied as set forth below. The results are in the table.

The mineral compound used in the product has no effect on product characteristics.

| Mineral Compound | Weight % | Product Characteristics |
|---|---|---|
| Calcium carbonate | 16.5[1] | Soft chew Acceptable processing No chalky taste Not sticky |
| Co-precipitate of aluminum hydroxide and magnesium carbonate | 10[1] | Soft chew Acceptable processing No chalky taste Not sticky |
| Kaolin (hydrated aluminum silicate) | 30 | Soft chew Difficult to process No chalky taste Not sticky |
| Magnesium-aluminum silicate | 25 | Dry granular chew Acceptable processing No chalky taste Not sticky |

[1]Additional nougat candy base added to compensate for decreased mineral content.

EXAMPLE 7

This Example demonstrates the availability of calcium ion from the inventive formulation of Example 1.

An in vitro dissolution test of the inventive product has been conducted. The results indicate the percent of calcium in solution at various times after start of the test is reported. In 60 minutes, 85.8% of the calcium present in the supplement is in solution.

| Time | % of Calcium in Solution |
|---|---|
| 30 min. | 59.2 |
| 45 min. | 70.6 |
| 60 min. | 85.8 |

All results are the average of six separate tests.

Dissolution test procedure:
*United States Pharmacopeia XX*, page 939, Mack Printing Co., Easton, Pa., 1980
Conditions:
 USP Apparatus 2
 Media: 900 ml simulated gastric fluid without enzymes
 Rotation Speed: 50 RPM.

Apparatus 2—Use the assembly from Apparatus 1, except that a paddle formed from a blade and a shaft is used as the stirring element.[4] The shaft, 10±0.5 mm in diameter, is positioned so that its axis is not more than 0.2 cm at any point from the vertical axis of the vessel, and rotates smoothly without significant wobble. The stirring blade, 3.0 mm to 5.0 mm thick, forms a section of a circle having a diameter of 83 mm, and is subtended by a parallel chords of 42±1 mm and 75±1 mm. The blade passes through the diameter of the shaft so that the bottom of the blade is flush with the bottom of the shaft, and the blade is positioned horizontally at the end of the rotating shaft so that the 42-mm edge is nearest the lowest inner surface of the vessel. The distance of 2.5±0.2 cm between the blade and the inside bottom of the vessel is maintained during the test. The metallic blade and shaft comprise a single entity that may be coated with a suitable fluorocarbon polymer. The dosage unit is allowed to sink to the bottom of the vessel before rotation of the blade is started. A small, loose piece of nonreactive material such as wire or glass helix may be attached to dosage units that would otherwise float.
[4] A suitable paddle is available commercially from Hanson Research Corp. and from Van-Kel Industries.

Apparatus 1—The assembly[1] consists of the following: a covered, 1000 ml vessel made of glass or other inert, transparent material[2]; a variable-speed drive; and a cylindrical basket. The vessels are immersed in a suitable water bath of any convenient size that permits holding the temperature at 37°±0.5° C. during the test and keeping the bath fluid in constant, smooth motion. No part of the assembly, including the environment in which the assembly is placed, contributes significant motion; agitation, or vibration beyond that due to the smoothly rotating stirring element. Apparatus that permits observation of the specimen and stirring element during the test is preferable. The vessel is cylindrical, with a spherical bottom. It is 16 cm to 17.5 cm high, its inside diameter is 10.0 cm to 10.5 cm, and its nominal capacity is 1000 ml. Its sides are flanged near the top. A fitted cover may be used to retard evaporation.[3] The shaft is positioned so that its axis is not more than 0.2 cm at any point from the vertical axis of the vessel. A speed-regulating device is used that allows the shaft rotation speed to be selected and maintained at the rate specified in the individual monograph, within ±4%.

[1] A suitable vessel is available commercially as Kimble Glass No. 33730, from laboratory supply houses, or as Elanco Products Division No. EQ-1900, from Eli Lilly and Co., P.O. Box 1750, Indianapolis, Ind. 46206. A suitable basket is available commercially from Hanson Research Corp., P.O. Box 35, Northridge, Calif. 91324, and from Van Kel Industries, P.O. Box 311 Chatham, N.J. 07928.
[2] The materials should not sorb, react, or interfere with the specimen being tested.
[3] If a cover is used, it provides surricient openings to allow ready insertion of the thermometer and withdrawal of specimens.

Assay Procedure for Calcium:
At each dissolution time period 50.0 ml of dissolution media is removed from the vessel and replaced with 50 ml of gastric fluid without enzymes. The 50.0 ml aliqnot is transferred to a suitable container. The solution is made basic by addition of 15 ml of 1N sodium hydroxide. 300 mg of hydroxy napthol blue triturate is added and the resultant solution titrated with standardized 0.05 M disodium ethylenediaminetetraacetate until the solution is deep blue. Each ml of 0.05 M disodium ethylenediaminetetraacetate is equivalent to 5.004 mg of calcium carbonate.

Calculation for percent in solution $$\frac{\text{mg CaCO}_3 \times 18}{1500} \times 100\% = \% \text{ Ca in solution}$$

The invention being thus described, it will be obvious that the same may be varied in many ways. Such variations are not to be regarded as a departure from the spirit and scope of the invention and all such modifications are intended to be included within the scope of the following claims.

We claim:

1. A chewable mineral supplement having a penetration hardness of 2 mm or more which comprises:
 from about 40 to about 85% by weight of a nougat candy base comprising:
  a syrup component comprising:
   (a) corn syrup having a dextrose equivalent from about 35 to about 55;
   (b) sugar such that the ratio of sugar to corn syrup is from about 1:1 to about 2:1; a whipped component comprising at least one whipping agent which introduces air into the nougat candy base to lower its specific weight and modify its texture;
 an edible polyol in an amount of from about 1.5 to about 6.0% by weight;
 a mineral compound in an amount of about 3 to about 40% by weight; and
 a water content of about 2 to about 4.5% by weight;
 all percents herein are by weight of the final chewable mineral supplement.

2. The chewable mineral supplement of claim 1 wherein said nougat candy base comprises:
 a syrup component in an amount of about 78 to about 99%, and
 a whipped component in an amount of about 1 to about 22%; all percentages are by weight of the nougat candy base.

3. The chewable mineral supplement of claim 2 wherein said syrup component comprises: by weight of the chewable mineral supplement,
 corn syrup in an amount of about 13 to about 41%,
 sugar in an amount of about 15 to about 53% such that the ratio of sugar to corn syrup is from about 1:1 to about 2:1.

4. The chewable mineral supplement of claim 2 wherein said whipped component comprises: by weight of the chewable mineral supplement,
 at least one whipping agent present in an amount of from about 0.1 to about 1%.

5. The chewable mineral supplement of claim 1 wherein said edible polyol is selected from the group consisting of propylene glycol, glycerin, polyethylene glycol and mixtures thereof.

6. The chewable mineral supplement of claim 1 wherein the edible polyol is glycerin.

7. The chewable mineral supplement of claim 1 wherein the edible polyol is present in an amount of from about 2.5 to about 4.5% by weight.

8. The chewable mineral supplement of claim 1 wherein said whipping agent is selected from the group consisting of egg albumin, modified milk protein, gelatin, milk protein, vegetable protein, and mixtures thereof.

9. The chewable mineral supplement of claim 1 which additionally contains a graining compound selected from the group consisting of fondant sugar, sugar, sorbitol crystals, lactose and mixtures thereof which is present in amounts from about 0.5 to about 4% by weight.

10. The chewable mineral supplement of claim 1 wherein the mineral compound is selected from a group consisting of salts of lithium, sodium, potassium, magnesium, calcium, phosphorous, iron, zinc, and mixtures thereof.

11. The chewable ineral supplement of claim 1 wherein the mineral compound is present in an amount of about 15 to about 40% by weight.

12. The chewable mineral supplement of claim 1 wherein the mineral compound is a calcium compound selected from the group consisting of calcium gluconate, calcium chloride, calcium lactate, calcium phosphate, monobasic calcium phosphate, dibasic calcium phosphate, tribasic calcium phosphate, calcium carbonate, calcium tartrate, calcium glycerophosphate, calcium levulinate, calcium hypophosphite, calcium sulfate, calcium gluceptate, calcium chelates, calcium amino acid chelate, ground limeatone, ground oysler shells, and mixtures thereof.

13. The chewable mineral supplement of claim 1 wherein the mineral compound is a lithium compound selected from the group consisting of organic and inorganic salts wherein the anion is chloride, carbonate, citrate, sulfate, bromide and mixtures thereof.

14. The chewable mineral supplement of claim 1 wherein the mineral compound is a sodium- compound selected from the group consisting of organic and inorganic salts of sodium wherein the anionic portion of the salt is acetate, ascorbate, bicarbonate, carbonate, chloride, citrate, hypophosphite, lactate, phosphate monobasic, phosphate dibasic, phosphate tribasic, sulfate, tartrate and mixtures thereof.

15. The chewable mineral supplement of claim 1 wherein the mineral compound is a potassium compound selected from the group consisting of inorganic and organic salts wherein the anionic portion of the salt is acetate, bicarbonate, bitartrate, bromide, carbonate, chloride, citrate, gluconate, phosphate monobasic, phosphate dibasic, phosphate tribasic, sulfate, tartrate and mixtures thereof.

16. The chewable mineral supplement of claim 1 wherein the mineral compound is a magnesium compound selected from the group consisting of organic and inorganic salts of magnesium wherein the anionic portion of the salt is acetate, carbonate, hydroxide, chloride, citrate, dibasic citrate, hydroxide, lactate, oxide, phosphate monobasic, phosphate dibasic, phosphate tribasic, trisilicate sulfate, as well as the composition formed as the co-precipitated gel of aluminum hydroxide and magnesium carbonate and mixtures thereof.

17. The chewable mineral supplement of claim 1 wherein the mineral compound is an iron compound selected from the group consisting of organic and inorganic salts and chelates of iron such as reduced iron, ferrous sulfate, iron ammonium citrate, ferrous carbonate, ferrous chloride, ferrous fumarate, ferroglycine sulfate, ferronacin, ferrous carbonate mass, ferrous carbonate saccharated, ferrous citrate, ferrous gluconate, ferrous lactate, ferrous sulfate, ferrous succinate, iron chelates, iron chelate with magnesium trisilicate and mixtures thereof.

18. The chewable mineral supplement of claim 1 wherein the mineral compound is a phosphorous compound selected from the group consisting of salts wherein the anionic portion is a phosphate and the cationic portion is sodium, potassium, magnesium, iron, calcium, lithium, zinc and mixtures thereof.

19. The chewable mineral supplement of claim 1 wherein the mineral compound is a zinc compound selected from the group consisting of inorganic and organic salts wherein the anionic portion of the salt is carbonate, chloride, citrate, and mixtures thereof.

20. The chewable mineral supplement of claim 3 wherein the sugar is sucrose, sorbitol, mannitol, liquid sugars, and mixtures thereof.

21. The chewable mineral supplement of claim 1 wherein the mineral compound is calcium carbonate.

22. The chewable mineral supplement of claim 1 further containing an absorption enhancer.

23. The chewable mineral supplement of claim 22 wherein said absorption enhancer is selected from the group consisting of vitamin D, lysine, arginine, lactose, vitamin D2, vitamin D3, calcitrol and mixtures thereof.

24. The chewable mineral supplement of claim 1 further containing an antiflatulent.

25. The chewable mineral supplement of claim 24 wherein said antiflatulent is simethicone.

26. A chewable mineral supplement having a penetration hardness of 2 mm or more, which comprises:
(A) from about 40 to about 85% by weight of a nougat candy base comprising,
  (1) a syrup component comprising:
    (a) corn syrup in an amount of about 13 to about 41% by weight having a dextrose equivalence from about 35 to about 55;
    (b) sugar in an amount of about 15 to about 53% such that the ratio of sugar to corn syrup is from about 1:1 to about 2:1,
  (2) a whipped component comprising at least one whipping agent present in an amount of from about 0.1 to about 1%;
(B) an edible polyol in an amount of from about 1.5 to about 6%;
(C) a mineral compound in an amount of about 3 to about 40%;
(D) a graining compound in an amount from about 0.5 to about 4%; and
(E) a water content of about 2 to about 4.5%; all percents herein are by weight of the final chewable mineral supplement.

27. The chewable mineral supplement of claim 26 further containing a fat component.

28. The chewable mineral supplement of claim 27 wherein said fat component is selected from the group consisting of fractionated fat, hydrogenated oils, partially hydrogenated oils, unsaturated oils, coconut oil, palm oil, palm kernal oil, cottonseed oil, safflower oil, sunflower oil, soy oil, corn oil and mixtures thereof.

29. A method for preparing a chewable mineral supplement having a penetration hardness of 2 mm or more, which comprises:
preparing a nougat candy base comprising:
a syrup component comprising:

(a) corn syrup having a dextrose equivalence from about 35 to about 55;
(b) sugar such that the ratio of sugar to corn syrup is from about 1:1 to about 2:1;
a whipped component comprising at least one whipping agent which introduces air into the nougat candy base to lower its specific weight and modify its texture;
admixing an edible polyol in an amount from about 1.5 to about 6.0% by weight to form a homogeneous mixture;
admixing a mineral compound in an amount of about 3 to about 40% by weight to form a homogeneous mixture; and
admixing a graining compound in an amount from about 0.5 to about 4% by weight to form a homogeneous mixture; and recovering the mixture;
all percents herein are by weight of the final chewable mineral supplement.

30. The method of claim 29 wherein the nougat candy base comprises by weight of the nougat candy base, a syrup component in an amount of about 78 to about 99%, and
a whipped component in an amount of about 1 to about 22%.

31. The method of claim 30 wherein said syrup component comprises, by weight of the chewable mineral supplement:
corn syrup in an amount of about 13 to about 41% having a dextrose equivalence from about 35 to about 55,
sugar in an amount of about 15 to about 53% such that the ratio of sugar to corn syrup is from about 1:1 to about 2:1, and
water in an amount up to about 40%.

32. A method for preparing said syrup component of claim 31 which comprises:
dissolving the corn syrup component and the sugar component in an amount of water such that the total water content is up to about 40% by weight of the corn syrup, sugar mixture,
cooking the corn syrup, sugar mixture until the resultant water content is from about 2 to about 6% by weight of the chewable mineral supplement.

* * * * *

UNITED STATES PATENT AND TRADEMARK OFFICE
CERTIFICATE OF CORRECTION

PATENT NO. : 4,582,709

DATED : Apr. 15, 1986

INVENTOR(S) : David Peters, et al

It is certified that error appears in the above-identified patent and that said Letters Patent is hereby corrected as shown below:

Column 1, line 61, delete "rapeutic" and insert therefor --therapeutic--.

Column 3, line 49, delete "syru" and insert therefor --syrup--.
Column 13, line 17, delete "ineral" and insert therefor --mineral--.
Column 13, line 29, delete "limeatone" and insert therefor --limestone--.
Column 13, line 29, delete "oysler" and insert therefor --oyster--.
Column 13, line 37, delete the "-" after "sodium".
Column 15, line 6, delete "whidh" and insert therefor --which--.

Signed and Sealed this

Fifteenth Day of July 1986

[SEAL]

Attest:

DONALD J. QUIGG

Attesting Officer

Commissioner of Patents and Trademarks